United States Patent [19]

Lazarof

[11] Patent Number: 5,087,199
[45] Date of Patent: * Feb. 11, 1992

[54] DENTAL IMPLANT AND METHOD OF USING SAME

[76] Inventor: Sargon Lazarof, 15215 Magnolia Blvd., #126, Sherman Oaks, Calif. 91403

[*] Notice: The portion of the term of this patent subsequent to Apr. 2, 2008 has been disclaimed.

[21] Appl. No.: 632,532

[22] Filed: Dec. 24, 1990

Related U.S. Application Data

[63] Continuation of Ser. No. 558,494, Jul. 27, 1990, Pat. No. 5,004,421.

[51] Int. Cl.$^5$ ............................................. A61C 8/00
[52] U.S. Cl. ......................................................... 433/173
[58] Field of Search ............... 433/169, 173, 174, 175, 433/176, 201.1

[56] References Cited

U.S. PATENT DOCUMENTS

| | | | |
|---|---|---|---|
| 2,721,387 | 10/1955 | Ashuckian | 433/176 |
| 3,579,831 | 5/1971 | Stevens et al. | 433/174 |
| 3,708,883 | 1/1973 | Flander | 433/174 |

Primary Examiner—John J. Wilson
Attorney, Agent, or Firm—James E. Brunton

[57] ABSTRACT

A dental implant that includes a tubular body portion which can be positively secured within a bore in a jaw bone by an expander mechanism, the tubular member being internally threaded so that a selected prosthetic component can be threadably connected to the tubular body portion immediately following securement of the tubular body to the bone.

11 Claims, 2 Drawing Sheets

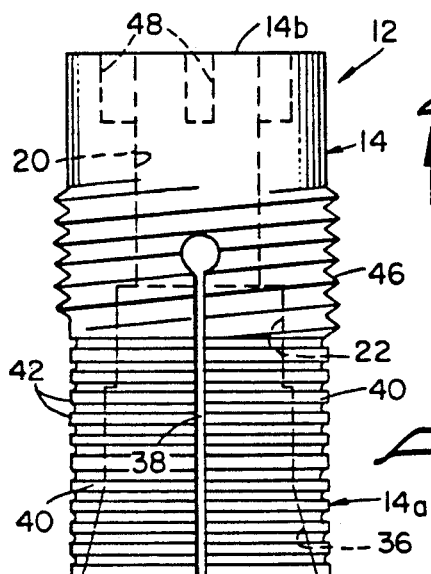
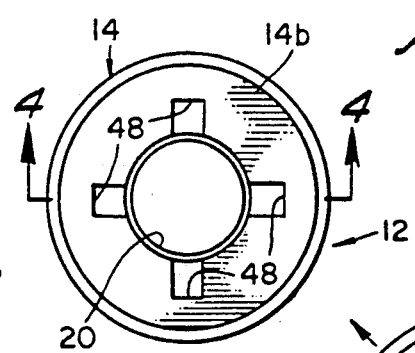
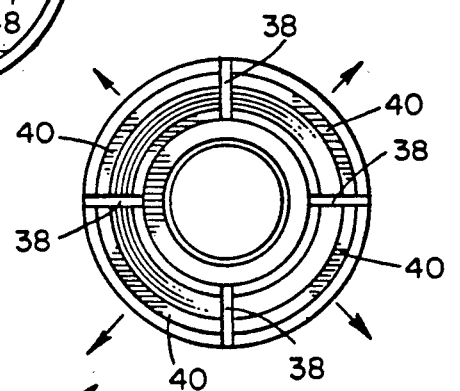
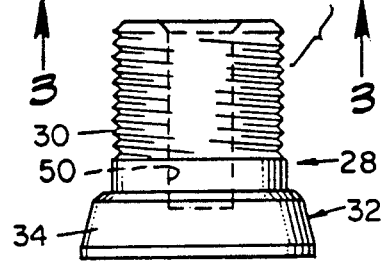
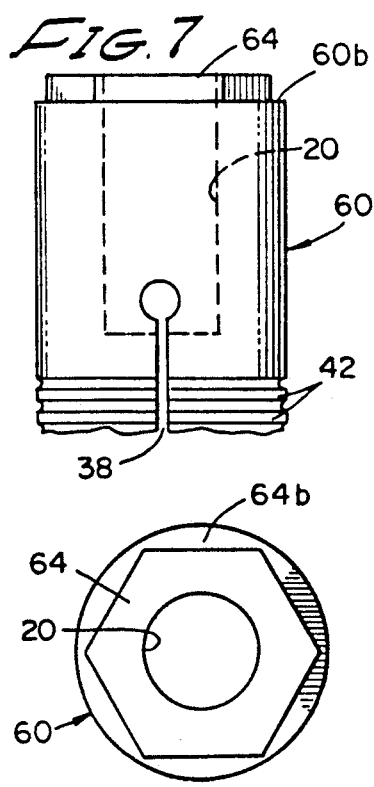
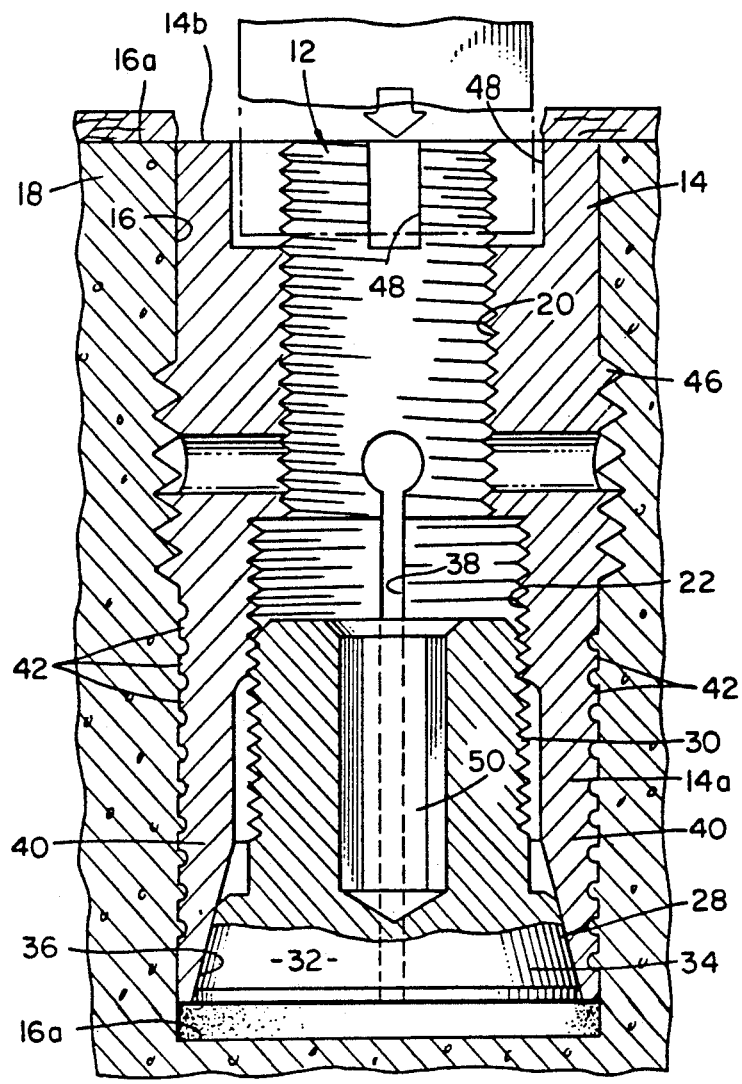

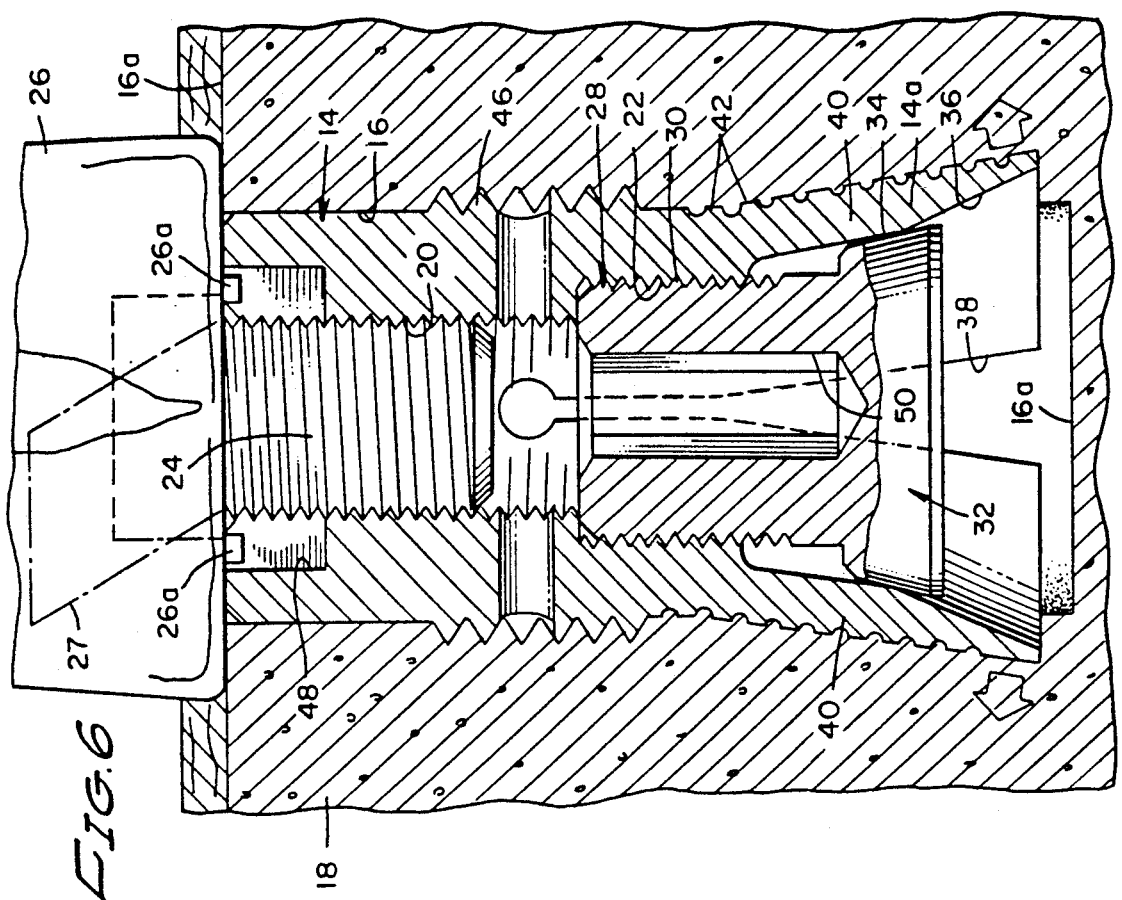
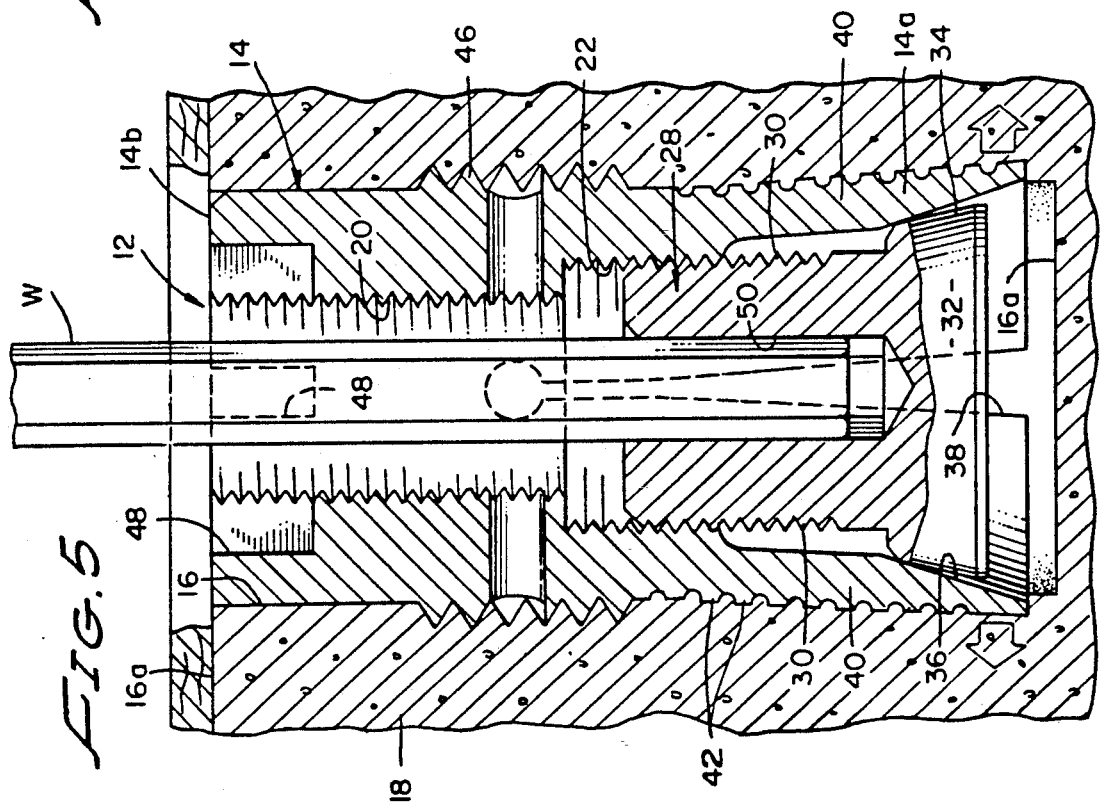

DENTAL IMPLANT AND METHOD OF USING SAME

This application is a continuation of application Ser. No. 07/558,494, filed July 27, 1990 now U.S. Pat. No. 5,004,421.

BACKGROUND OF THE INVENTION

1. Field of the Invention

The present invention relates generally to dental implants. More particularly, the invention concerns a dental implant which includes a tubular body portion that can be positively secured within a bore in a jaw bone by an expander mechanism, the tubular member being threaded so that a selected prosthetic component can be threadably connected to the tubular body portion immediately following securement of the tubular body to the bone.

2. Discussion of the Invention

Introduction

Dental implants of the character receivable within a bore provided in the jaw bone are old in the art. Typically such implants comprise an apertured body portion which is emplaced within a bore drilled in the bone. The body portion is designed so that during a period of about four to six months after its emplacement within the bore, bone tissue will grow into the apertures so as to secure the body portion of the implant in place within the bone bore. Following this four to six month period, an artificial tooth or other prosthetic component is secured to the body portion. This procedure is undesirable in several respects. In the first place, the procedure is protracted and requires multiple visits to the oral surgeon. Secondly, during the extended period of time required for the bone tissue to grow into and around the implant, the patient is left with an uncomfortable and unsightly cavity where the prosthetic component, such as an artificial tooth will eventually go. Additionally, this procedure does not always provide adequate anchoring of the implant to the jaw bone so that in time the implant can loosen.

In order to overcome the drawbacks of the standard procedure described in the preceding paragraph, several types of implants using mechanical locking means for securing the implant in place within the bore in the jaw bone have been suggested. Exemplary of such devices is the device described in Flander U.S. Pat. No. 3,708,883.

The Flander device comprises an implant which has an elongated tubular body provided with an outer anchoring portion which includes spreadable portions having projections adapted to be pressed into the bone. These portions are mechanically spread apart by an elongated spreader screw which extends through the tubular body. A nut mounted on the outer end of the tubular body is threaded onto the spreader screw to pull it outwardly causing the spreadable anchor portions to spread a part from each other and to press the projections formed thereon into the bone. The artificial tooth is then bonded to the nut and to a portion of the spreader screw.

The implant of the present invention also makes use of mechanical securement means, but unlike the Flander device, the device includes means by which selected dental prosthetics of standard design can be threadably interconnected. In this way, angular corrections of the prosthetic, such as an artificial tooth, can readily be made. Further, in one form of the device of the invention, the implant is positively secured within the bore in the bone by two separate, but cooperating securement mechanisms. The first securement mechanism comprises self-tapping, external threads provided on the tubular body of the device which are threaded into the bone by rotating the device in a first direction. The second, cooperating securement mechanism comprises a plurality of bone penetrating anchor blades formed on the skirt portion of the tubular body which are moved into a bone engagement position only after the implant has been securely threaded into the bone. In this embodiment of the invention, the anchor blades are moved into the bone engagement configuration by rotating a threaded expander member also in a first direction. However, because the threads on the expander member are opposite to the threads on the tubular body, rotational forces exerted on the expander member continuously urges the implant in a tightening direction. In other words, as the anchor blades are urged outwardly, the implant is continuously urged into threaded engagement with the bone. This novel, double locking approach permits the selected prosthetic component to be connected to the implant immediately without the patient having to return to the oral surgeon a second time.

In an alternate form of the invention, the tubular member is provided with means for locking it against rotation as the anchor blades are cammed outwardly into the bone. In this form of the invention, means are also provided for threadably connecting a wide variety of dental prosthetics to the implant immediately after the implant is secured to the bone.

SUMMARY OF THE INVENTION

It is an object of the present invention to provide a dental implant which can be very easily secured within a bore provided in the jaw bone of the patient in such a positive fashion that growth of bone tissue about the implant is not a prerequisite to the interconnection thereto of a selected prosthetic component. Accordingly, the drilling of the bone, the securement of the implant, and the affixing of the prosthetic component can all be accomplished in a single session with the oral surgeon.

It is another object of the invention to provide an implant of the aforementioned character in which means are provided for the threadable interconnection thereto of a number of different types of standard prosthetic components, such as dental crowns, plates, anchors and the like. In this way precise angular correction can be made to accommodate misalignment of the implant that might occur due to irregularities in the configuration of the jaw bone.

Another object of the invention is to provide an implant, which itself can be retrieved, or from which the prosthetic component can be readily removed at a later date if such action is required.

A further object of the invention is to provide an implant of the type described in the preceding paragraphs in which both the implant and the prosthetic component can be securely locked against rotational movement tending to retract the implant from the bone.

Yet another object of the invention is to provide an implant of the character which insures that titanium metal is present between the patients gum and a prosthetic such as a crown.

Still another object of the invention to provide a dental implant in which the implant is positively secured within the bone bore by means of two cooperating securement mechanisms so that once in place the implant cannot work loose with the passage of time.

Another object of the invention is to provide a dental implant of the character described which can be secured to the bone with a minimum surgical procedure and in a manner to avoid undesirable trauma to the patient.

Yet another object of the invention is to provide a dental implant which can be quickly and easily installed by a method which reduces discomfort to the patient to an absolute minimum.

Another object of the invention is to provide a method of the character described in the preceding paragraph by which the complete installation of the implant and the prosthetic component can be accomplished during a single visit to the oral surgeon.

In summary, these and other objects of the invention can be achieved by installing within a bore in the jaw bone an implant which includes a tubular body having longitudinally spaced first and second internal threads, the first internal threads being adapted to threadably receive a selected prosthetic component of standard design. The tubular body includes a skirt portion having four circumferentially spaced anchoring segments which are movable from a first retracted position to a second expanded, bone-penetrating position by an expander member threadably received within the second internal threads of the tubular body. The tubular body is also provided with means for preventing rotation of the tubular member as the expander member is threaded into the tubular member so that the implant can be precisely positioned within the bore in the jaw bone.

BRIEF DESCRIPTION OF THE DRAWINGS

FIG. 1 is an exploded side elevational view of one form of dental implant of the present invention.

FIG. 2 is a top view of the implant.

FIG. 3 is a view taken along lines 3—3 of FIG. 1.

FIG. 4 is a cross-sectional view of the implant taken along lines 4—4 of FIG. 2 and showing the implant in position within a bore provided in the jaw bone of the patient.

FIG. 5 is a cross-sectional view similar to FIG. 4 but showing an allen wrench inserted into the inner cavity of the expander member of the apparatus and showing the expander member moving inwardly of the tubular member of the device and starting to force the anchor blades outwardly into engagement with the bone.

FIG. 6 is a cross-sectional view similar to FIG. 5 but showing the expander member moved inwardly of the tubular member to a position wherein the anchor blades are moved outwardly to the maximum extent. Also illustrated in FIG. 6 is the attachment to the implant of a prosthetic component shown here as a dental crown.

FIG. 7 is a fragmentary, cross-sectional view similar to FIG. 1 showing an alternate form of the invention having a gripping means provided in the form of a hexagonally shaped upper portion.

FIG. 8 is a top view of the embodiment of the invention shown in FIG. 7.

DESCRIPTION OF THE INVENTION

Referring to the drawings and particularly to FIGS. 1 through 4, one embodiment of the dental implant of the present invention is there shown and generally designated by the numeral 12. As best seen by referring to FIGS. 1 and 4, the dental implant comprises an elongated tubular body 14 which is receivable within a bore 16 provided in the jaw bone 18 of the patient. (FIG. 4). Body 14 is provided with first and second internal threads 20 and 22, the first internal threads 20 being adapted to threadably receive a threaded shank portion 24 of a prosthetic component shown in FIG. 6 as a dental crown 26.

Tubular member 14 includes a skirt portion 14a movable from a first retracted position shown in FIG. 4 to a second expanded position shown in FIG. 6. To move the skirt portion 14a into the second expanded position, there is provided expander means shown in the drawings as an expander assembly 28. Referring to FIG. 1, expander assembly 28 can be seen to comprise an externally threaded body portion 30 and a generally frusto-conically shaped skirt engaging portion 32. Portion 32 includes inwardly sloping, or inclined, sidewalls 34 which are adapted to engage inwardly sloping, or inclined, sidewalls 36 provided on skirt portion 14a of tubular member 14.

As best seen by referring to FIGS. 1 and 3, skirt portion 14a is provided with four circumferentially spaced elongated slits 38 which define four, separately-movable bone anchor segments 40 each having bone penetrating means provided here as a series of longitudinally spaced, blade-like bone penetrating protuberances 42. In a manner presently to be described, as the expander means is drawn into tubular member 14, the anchor blades 14a will be expanded outwardly so that penetrating protuberances 42 slice into the bone in a manner to securely lock the tubular member within bore 16.

Forming an important aspect of the device of the present invention, is a provision of means for resisting rotation of the tubular body 14 within the bore 16 upon the exertion of a rotational force tending to retract the tubular body from the bore. In the form of the invention illustrated in FIGS. 1 through 6, this means for resisting rotation is provided in the form of external threads 46 provided on tubular member 14. As best seen in FIG. 4, external threads 46 are of a diameter slightly larger than the diameter of bore 16 and are self-tapping so that they will thread into the bone 18 upon rotation of the tubular body in a selected first direction. To enable positive rotation of the tubular body in the selected direction, the upper surface 14b of tubular body 14 is provided with four circumferentially spaced spanner wrench slots 48. Slots 48 are adapted to receive a spanner wrench of conventional design so that upon exertion of rotational forces in a first direction, threads 46 can be smoothly and effortlessly threaded into the bone 18 surrounding the drilled bore 16. As indicated in FIG. 4, tubular body 14 is threaded into bore 16 until it bottoms out against the lower surface 16a of the bore in the manner illustrated in. In this position, the upper surface 14b of the tubular member is substantially flush with the upper surface 16a of the jaw bone (FIG. 4). With the tubular member thus seated within the bore 16, external threads 46 effectively function to resist counter-rotational movement tending to extract tubular member 14 from the bore.

Turning again to FIGS. 1 and 4, the externally threaded body portion 30 of the expander means is provided with a socket 50 which is configured to closely receive the shank of a conventional allen wrench. When an allen wrench W is inserted into socket 50 in the manner shown in FIG. 5, rotational forces exerted on the allen wrench in a first direction will cause body portion 30 of the expander means to move inwardly of the internally threaded skirt portion 14a of tubular member 14. This result is achieved because internal threads 22 are of a hand opposite to the hand of external threads 46. More specifically, if threads 46 are right-handed threads so that tubular body member 14 is threaded into bore 16 by the exertion of forces in a clockwise direction, then threads 22 will be left-hand threads rather than right-hand threads. With this construction, the exertion of clockwise rotational forces on the allen wrench W will cause body portion 30 of the expander means to be progressively threaded inwardly of tubular body 14 causing inclined walls 34 of the expander means to pressurally engage the inclined walls 36 of the skirt portions 14a thereby causing anchor blades 40 to move outwardly in the direction shown by the lower arrows in FIGS. 5 and 6. It is apparent that with this opposite hand thread arrangement, forces exerted on the allen wrench tending to draw the expander means into the tubular member will function to rotate tubular member 14 in a tightening rather than loosening direction.

Once the tubular member is secured within the bore 16 in the jaw bone, the threaded shank 24 of the prosthetic component can be threadably mated with the first internal threads 20 provided on the tubular member 14. As previously mentioned, the prosthetic component can take several forms including a dental crown of the character shown in FIG. 6. The prosthetic component may also take the form of a ball over denture attachment, a pre-angled fixed prosthetic abutment, an impression post, a waxing post, and any number of like prosthetic components of the character well known skilled in the dental arts. As indicated by the phantom lines in FIG. 16, the prosthetic component can be provided with an angularly extending stem 27. By selecting the proper angle of the stem, any angular misalignment of the tubular member relation to the jaw bone can be readily accommodated. This provides a substantial advantage over non-adjustable stem cam functions as provided by the earlier described Flander device. Additionally, unlike the Flander device, the prosthetic component can be easily removed. Further, unlike the Flander construction, a metal such as titanium resides between the patients' sum and the crown.

Referring now to FIGS. 7 and 8, an alternate form of the tubular body of the device of the present invention is there shown and designated by the numeral 60. This member is identical to tubular body 14 save that external threads 46 are absent as are the spanner wrench slots 48. Like numerals are used in FIGS. 7 and 8 to designate like elements shown in FIGS. 1 through 6. In this second embodiment of the invention, the means for resisting rotation of the tubular body within the bore 16 is provided in the form of a generally hexagonal shaped portion 64 formed proximate the top 60b of the tubular member. Hexagonal portion 64 provides a means for engagement of the tubular member with a conventional wrench so as to resist rotation of the tubular member in either a clockwise or counter-clockwise direction during the time that the expander means is being threaded into the tubular body so as to cam the anchor blades 40 outwardly into seating engagement with the bone surrounding the bore 16. When the device is provided with the wrench engaging hexagonal portion 64, second threads 22 which receive the expander means need not be of an opposite hand from threads 20 which receive the threaded shank portion of the prosthetic component, which also is typically provided with right-hand threads.

Hexagonal portion 64 can also provide anti-rotation means for the prosthetic component if the component is constructed with an appropriately shaped cavity on its lower surface which is adapted to fit over portion 64. Similarly, in the previously described form of the invention, the prosthetic component can be provided with downwardly extending protuberences 26a (FIG. 6) adapted to fit within spanner wrench slots 48 to prevent rotation of the component in a loosening direction.

Use of either of the implants of the character described herein comprises the steps of drilling the jaw bone to provide a bore of a selected diameter; emplacing tubular member 14 or 60 into the bore; and rotating the expander means in a direction to threadably mate the external threads 30 with the internal threads 22 of the tubular member so as to force the anchor blades outwardly into the bone. When the device of the second embodiment of the invention is used, the tubular member is held against rotation by gripping the hexagonal head 64 with a suitable wrench. When the first form of the device is used, the thread hands of threads 46, 30 and 22 are selected so that during expansion of the anchor blades, tightening forces are continuously applied to the tubular member. After the tubular member is thus anchored in place, the appropriate prosthetic component is threadably connected to the tubular member. As previously mentioned, if the tubular member is angularly misaligned with the jaw bone, a prosthetic component having an appropriately angled connector shank can be used to correct the situation.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention as set forth in the following claims.

I claim:

1. A dental implant for securement within a bore provided in the jaw bone of a patient, said implant comprising:
   (a) an elongated hollow body receivable within the bore provided in the jaw bone of the patient, said body having threads and including means for orienting a prosthetic component with respect to said hollow body, said hollow body further including:
      (i) means for resisting rotation of said hollow body within the bore upon the exertion of a rotational force tending to retract said hollow body from the bore;
      (ii) a movable portion movable from a first retracted position to a second expanded position; and
   (b) expander means including a shank portion having external threads mateable with said threads of said body for moving said skirt portion from said first retracted position to said second expanded position upon rotation of said shank portion.

2. A dental implant as defined in claim 1 in which said movable portion includes a skirt portion comprising at least one segments anchor segment movable from a first retracted position to a second expanded position.

3. A dental implant as defined in claim 2 in which said skirt portion includes an inclined internal surface and in which said expander means comprises a skirt engaging portion having an inclined external surface movable into engagement with said inclined internal surface of said skirt portion upon rotation of said shank portion in said first direction.

4. A dental implant as defined in claim 3 in which said shank portion includes allen wrench engaging means for receiving an allen wrench for imparting rotational movement to said shank portion in said first direction.

5. A dental implant as defined in claim 3 in which said hollow body includes an upper surface having spanner wrench engaging means for receiving a spanner wrench for imparting rotation to said body in a first direction.

6. A dental implant as defined in claim 3 in which said segments of said skirt portion include bone penetrating means for penetrating the bone of the patient upon movement of said segment into said second expanded position.

7. A dental implant as defined in claim 1 in which said means for resisting rotation of said hollow body comprises external threads provided on said hollow body, said threads being of a hand opposite to said second internal threads.

8. A method of securing a prosthetic component to a patient's jaw bone using a dental implant comprising an elongated tubular body having means for resisting rotation thereof, means for connecting a prosthetic component thereto, internal threads and a skirt portion movable from a first retracted position to a second, bone penetrating expanded position and expander means, including an externally threaded portion mateable with said internal threads of said tubular body for moving said skirt portion toward said second position, said method comprising the steps of:

(a) drilling in the jaw bone a bore of diameter slightly larger than the external diameter of said tubular body of said implant;

(b) placing said tubular body into the bore;

(c) rotating said expander means in a direction to threadably mate said external threads of said externally threaded portion of said expander means with said internal threads of said tubular body so as to move said skirt portion into said second bone penetrating, expanded position; and (d) connecting said prosthetic component to said tubular body portion.

9. A method as defined in claim 8 including the further step of gripping said means for resisting rotation to prevent rotation of said tubular body.

10. A method as defined in claim 8 in which said prosthetic component comprises a dental crown.

11. A method as defined in claim 10 in which said prosthetic component further comprises a crown supporting shank portion extending at an angle with respect to the longitudinal axis of said tubular body member.

* * * * *